United States Patent [19]

Albaugh

[11] Patent Number: 5,182,290

[45] Date of Patent: Jan. 26, 1993

[54] CERTAIN OXAZOLOQUINOLINONES; A NEW CLASS OF GABA BRAIN RECEPTOR LIGANDS

[75] Inventor: Pamela Albaugh, Clinton, Conn.

[73] Assignee: Neurogen Corporation, Branford, Conn.

[21] Appl. No.: 750,464

[22] Filed: Aug. 27, 1991

[51] Int. Cl.$^5$ .................. C07D 498/04; C61K 31/47
[52] U.S. Cl. .................. 514/293; 514/232.8; 514/253; 514/254; 544/126; 544/361; 546/83
[58] Field of Search .................. 546/83; 544/361, 126; 514/293, 232.8, 254, 253

[56] References Cited

U.S. PATENT DOCUMENTS 4,713,383  12/1987  Francis et al. .................. 514/267

FOREIGN PATENT DOCUMENTS 168309A  1/1986  European Pat. Off. .................. 546/83

OTHER PUBLICATIONS

Bull. Chem. Soc. Japan, 50:3075 (Merchant and Shirali, 1977) A Simple Method for the Synthesis of 5-Methyloxazolo [4,5-C]Quinolin-4(5H)-one.

Ponomarev, O. A., et al. (Khar'K Gos. Univ. Kharkov, USSR). UKr. Khim. 2h, (Russ Ed.) 1990, 56(3), 272-6 (Russ.) Chem. Ab. 113:132057 K.

Ponomarev, O. A., et al. (Khar'K Gos. Univ., Kharkov, USSR). Teor. EKsp. Khim, 1990, 26(6) 644-50 (Russ.) Chem Ab. 115:7962s.

Ponomarev, O.A., et al. (Khar'K Gos. Univ. Kharkov, USSR). Zh Fiz Khim. 1990 64(10), 2723-9 (Russ) Chem. Ab. 114:100938c.

Primary Examiner—C. Warren Ivy
Assistant Examiner—Barbara Twardzik
Attorney, Agent, or Firm—Allegretti & Witcoff, Ltd.

[57] ABSTRACT

This invention encompasses compounds of the formula:

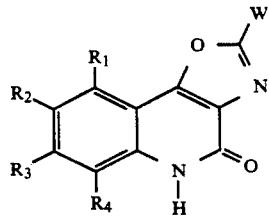

and the pharmaceutically acceptable non-toxic salts thereof wherein $R_1$, $R_2$, $R_3$, $R_4$, and W are variables These compounds are highly selective agonists, antagonists or inverse agonists for $GABA_a$ brain receptors or prodrugs thereof and are useful in the diagnosis and treatment of anxiety, sleep and seizure disorders, overdose with benzodiazepine drugs, and enhancement of memory.

22 Claims, 1 Drawing Sheet

Compound 1

Compound 2

Compound 4

CERTAIN OXAZOLOQUINOLINONES; A NEW CLASS OF GABA BRAIN RECEPTOR LIGANDS

BACKGROUND OF THE INVENTION

1. Field of the Invention

This invention relates to certain oxazoloquinolinones which selectively bind to GABAa receptors. This invention also relates to pharmaceutical compositions comprising such compounds. It further relates to the use of such compounds in treating anxiety, sleep and seizure disorders, and overdoses of benzodiazepine-type drugs, and enhancing alertness. The interaction of oxazoloquinolinones of the invention with a GABA binding site, the benzodiazepines (BDZ) receptor, is described. This interaction results in the pharmacological activities of these compounds.

2. Description of the Related Art

γ-Aminobutyric acid (GABA) is regarded as one of the major inhibitory amino acid transmitters in the mammalian brain. Over 30 years have elapsed since its presence in the brain was demonstrated (Roberts and Frankel, J. Biol. Chem 187: 55-63, 1950; Udenfriend, J. Biol. Chem. 187: 65-69, 1950). Since that time, an enormous amount of effort has been devoted to implicating GABA in the etiology of seizure disorders, sleep, anxiety and cognition (Tallman and Gallager, Ann. Rev. Neuroscience 8: 21-44, 1985). Widely, although unequally, distributed through the mammalian brain, GABA is said to be a transmitter at approximately 30% of the synapses in the brain. In most regions of the brain, GABA is associated with local inhibitory neurons and only in two regions is GABA associated with longer projections. GABA mediates many of its actions through a complex of proteins localized both on cell bodies and nerve endings; these are called GABAa receptors. Postsynaptic responses to GABA are mediated through alterations in chloride conductance that generally, although not invariably, lead to hyperpolarization of the cell. Recent investigations have indicated that the complex of proteins associated with postsynaptic GABA reponses is a major site of action for a number of structurally unrelated compounds capable of modifying postsynaptic responses to GABA. Depending on the mode of interaction, these compounds are capable of producing a spectrum of activities (either sedative, anxiolytic, and anticonvulsant, or wakefulness, seizures, and anxiety).

1,4-Benzodiazepines continue to be among the most widely used drugs in the world. Principal among the benzodiazepines marketed are chlordiazepoxide, diazepam, flurazepam, and triazolam. These compounds are widely used as anxiolytics, sedative-hypnotics, muscle relaxants, and anticonvulsants. A number of these compounds are extremely potent drugs; such potency indicates a site of action with a high affinity and specificity for individual receptors. Early electrophysiological studies indicated that a major action of benzodiazepines was enhancement of GABAergic inhibition. The benzodiazepines were capable of presynaptic inhibition of a monosynaptic ventral root reflex, a GABA-mediated event (Schmidt et al., 1967, Arch. Exp. Path. Pharmakol. 258: 69-82). All subsequent electrophysiological studies (reviewed in Tallman et al. 1980, Science 207:274-81, Haefley et al., 1981, Handb. Exptl. Pharmacol. 33: 95-102) have generally confirmed this finding, and by the mid-1970s, there was a general consensus among electrophysiologists that the benzodiazepines could enhance the actions of GABA.

With the discovery of the "receptor" for the benzodiazepines and the subsequent definition of the nature of the interaction between GABA and the benzodiazepines, it appears that the behaviorally important interactions of the benzodiazepines with different neurotransmitter systems are due in a large part to the enhanced ability of GABA itself to modify these systems. Each modified system, in turn, may be associated with the expression of a behavior.

Studies on the mechanistic nature of these interactions depended on the demonstration of a high-affinity benzodiazepine binding site (receptor). Such a receptor is present in the CNS of all vertebrates phylogenetically newer than the boney fishes (Squires and Braestrup 1977, Nature 166: 732-34, Mohler and Okada, 1977, Science 198: 854-51, Mohler and Okada, 1977, Br: J. Psychiatry 133: 261-68). By using tritiated diazepam, and a variety of other compounds, it has been demostrated that these benzodiazepine binding sites fulfill many of the criteria of pharmacological receptors; binding to these sites in vitro is rapid, reversible, stereospecific, and saturable. More importantly, highly significant correlations have been shown between the ability of benzodiazepines to displace diazepam from its binding site and activity in a number of animal behavioral tests predictive of benzodiazepine potency (Braestrup and Squires 1978, Br. J. Psychiatry 133: 249-60, Mohler and Okada, 1977, Science 198: 854-51, Mohler and Okada, 1977, Br. J. Psychiatry 133: 261-68). The average therapeutic doses of these drugs in man also correlate with receptor potency (Tallman et al. 1980, Science 207: 274-281).

In 1978, it became clear that GABA and related analogs could interact at the low affinity (1 mM) GABA binding site to enhance the binding of benzodiazepines to the clonazepan-sensitive site (Tallman et al. 1978, Nature, 274: 383-85). This enhancement was caused by an increase in the affinity of the benzodiazepine binding site due to occupancy of the GABA site. The data were interpreted to mean that both GABA and benzodiazepine sites were allosterically linked in the membrane as part of a complex of proteins. For a number of GABA analogs, the ability to enhance diazepam binding by 50% of maximum and the ability to inhibit the binding of GABA to brain membranes by 50% could be directly correlated. Enhancement of benzodiazepine binding by GABA agonists is blocked by the GABA receptor antagonist (+) bicuculline; the stereoisomer (−) bicuculline is much less active (Tallman et al., 1978, Nature, 274: 383-85).

Soon after the discovery of high affinity binding sites for the benzodiazepines, it was discovered that a triazolopyridazine could interact with benzodiazepine receptors in a number of regions of the brain in a manner consistent with receptor heterogeneity or negative cooperativity. In these studies, Hill coefficients significantly less than one were observed in a number of brain regions, including cortex, hippocampus, and striatum. In cerebellum, triazolopyridazine interacted with benzodiazepine sites with a Hill coefficient of 1 (Squires et al., 1979, Pharma, Biochem. Behav. 10: 825-30, Klepner et al. 1979, Pharmacol. Biochem. Behav. 11: 457-62). Thus, multiple benzodiazepine receptors were predicted in the cortex, hippocampus, striatum, but not in the cerebellum.

Based on these studies, extensive receptor autoradiographic localization studies were carried out at a light microscopic level. Although receptor heterogeneity has been demonstrated (Young and Kuhar 1980, J. Pharmacol. Exp. Ther. 212: 337–46, Young et al., 1981 J. Pharmacol Exp. ther 216: 425–430, Niehoff et al. 1982, J. Pharmacol. Exp. Ther. 221: 670–75), no simple correlation between localization of receptor subtypes and the behaviors associated with the region has emerged from the early studies. In addition, in the cerebellum, where one receptor was predicted from binding studies, autoradiography revealed heterogeneity of receptors (Niehoff et al., 1982, J. Pharmacol. Exp. Ther. 221: 670–75).

A physical basis for the differences in drug specificity for the two apparent subtypes of benzodiazepine sites has been demonstrated by Sieghart and Karobath, (1980, Nature 286: 285–87). Using gel electrophoresis in the presence of sodium dodecyl sulfate, the presence of several molecular weight receptors for the benzodiazepines has been reported. The receptors were identified by the covalent incorporation of radioactive flunitrazepam, a benzodiazepine which can covalently label all receptor types. The major labeled bands have molecular weights of 50,000 to 53,000, 55,000, and 57,000 and the triazolopyridazines inhibit labeling of the slightly higher molecular weight forms (53,000, 55,000, 57,000) (Seighart et al. 1983, Eur. J. Pharmacol. 88: 291–99).

At that time, the possibility was raised that the multiple forms of the receptor represent "isoreceptors" or multiple allelic forms of the receptor (Tallman and Gallager 1985, Ann. Rev. Neurosci. 8, 21–44). Although common for enzymes, genetically distinct forms of receptors have not generally been described. As we begin to study receptors using specific radioactive probes and electrophoretic techniques, it is almost certain that isoreceptors will emerge as important in investigations of the etiology of psychiatric disorders in people.

The GABAa receptor subunits have been cloned from bovine and human cDNA libraries (Schoenfield et al., 1988; Duman et al., 1989). A number of distinct cDNAs were identified as subunits of the GABAa receptor complex by cloning and expression. These are categorized into $\mu$, $\beta$, g, d,  , and provide a molecular basis for the GABAa receptor heterogeneity and distinctive regional pharmacology (Shivvers et al., 1980; Levitan et al., 1989). The $\gamma$ subunit appears to enable drugs like benzodiazepines to modify the GABA responses (Pritchett et al., 1989). The presence of low Hill coefficients in the binding of ligands to the GABAa receptor indicates unique profiles of subtype specific pharmacological action.

Drugs that interact at the GABAa receptor can possess a spectrum of pharmacological activities depending on their abilities to modify the actions of GABA. For example, the beta-carbolines were first isolated based upon their ability to inhibit competitively the binding of diazepam to its binding site (Nielsen et al., 1979, Life Sci. 25: 679–86). The receptor binding assay is not totally predictive about the biological activity of such compounds; agonists, partial agonists, inverse agonists, and antagonists can inhibit binding. When the beta-carboline structure was determined, it was possible to synthesize a number of analogs and test these compounds behaviorally. It was immediately realized that the beta-carbolines could antagonize the actions of diazepam behaviorally (Tenen and Hirsch, 1980, Nature 288: 609–10). In addition to this antagonism, beta-carbolines possess intrinsic activity of their own opposite to that of the benzodiazepines; they become known as inverse agonists.

In addition, a number of other specific antagonists of the benzodiazepine receptor were developed based on their ability to inhibit the binding of benzodiazepines. The best studied of these compounds is an imidazodiazepine, (Hunkeler et al., 1981, Nature 290: 514–516). This compound is a high affinity competitive inhibitor of benzodiazepine and beta-carboline binding and is capable of blocking the pharmacological actions of both these classes of compounds. By itself, it possesses little intrinsic pharmacological activity in animals and humans (Hunkeler et al., 1981, Nature 290: 514–16; Darragh et al., 1983, Eur. J. Clin. Pharmacol. 14: 569–70). When a radiolabeled form of this compound was studied (Mohler and Richards, 1981, Nature 294: 763–65), it was demonstrated that this compound would interact with the same number of sites as the benzodiazepines and beta-carbolines, and that the interactions of these compounds were purely competitive. This compound is the ligand of choice for binding to GABAa receptors because it does not possess receptor subtype specificity and measures each state of the receptor.

The study of the interactions of a wide variety of compounds similar to the above has led to the categorizing of these compounds. Presently, those compounds possessing activity similar to the benzodiazepines are called agonists. Compounds possessing activity opposite to benzodiazepines are called inverse agonists, and the compounds blocking both types of activity have been termed antagonists. This categorization has been developed to emphasize the fact that a wide variety of compounds can produce a spectrum of pharmacological effects, to indicate that compounds can interact at the same receptor to produce opposite effects, and to indicate that beta-carbolines and antagonists with intrinsic anxiogenic effects are not synonymous. A biochemical test for the pharmacological and behavioral properties of compounds that interact with the benzodiazepine receptor continues to emphasize the interaction with the GABAergic system. In contrast to the benzodiazepines, which show an increase in their affinity due to GABA (Tallman et al., 1978, Nature 274: 383–85, Tallman et al., 1980, Science 207: 274–81), compounds with antagonist properties show little GABA shift (i.e., change in receptor affinity due to GABA) (Mohler and Richards 1981, Nature 294: 763–65), and the inverse agonists actually show a decrease in affinity due to GABA (Braestrup and Nielson 1981, Nature 294: 472–474). Thus, the GABA shift predicts generally the expected behavioral properties of the compounds.

Various compounds have been prepared as benzodiazepine agonists and antagonists. For example, U.S. Pat. Nos. 4,312,870 and 4,713,383, and European Patent Application EP 181,282 disclose assorted compounds useful in treating anxiety or depression. U.S. Pat. No. 4,713,383 teaches compounds of the formula:

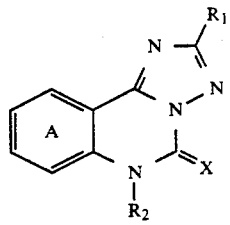

wherein R₁=(un)substituted Ph, (dihydro)furanyl, tetrahydrofuranyl, (dihydro)thienyl, tetrahydrothienyl, pyranyl, ribofuranosyl, all C-attached; R₂=H, alkyl; X=O, S, R₃N; R₃=H, alkenyl, alkynyl, C₃₋₂₀ cycloakyl, (un)substituted alkyl, aryl, aralkyl, where aryl is Ph, pyridinyl, thienyl, furanyl; ring A may be substituted by alkyl, alkoxy, halo, amino, alkylthio, etc.

European Patent Application EP 181,282 discloses compounds of the formula:

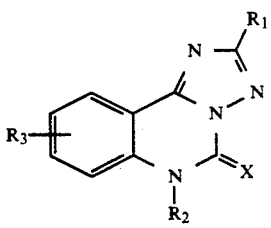

wherein R₁=(substituted) Ph or heterocycle; R₂=H, alkyl, alkenyl, hydroxyalkyl, aralkyl, aralkenyl, aryl; R₃=H, alkyl, alkoxy, HO, halo, F₃C, O₃N, H₂N, alkylthio, alkylsulfinyl, alkylsulfonyl, aralkoxy; X=O, S, NR₄; and R₄=H, alkyl, aralkyl, cycloalkyl, alkenyl, alkynyl, aryl, (substituted) aminoalkyl, hydroxyalkyl.

U.S. Pat. No. 4,312,870 teaches compounds of formulas:

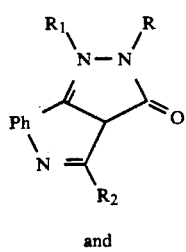

i and

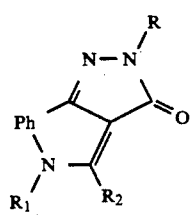

ii where Ph is 1,2-phenylene, unsubstituted or substituted by up to 3 identical or different members selected from lower alkyl, lower alkoxy, lower alkylthio, hydroxy, halogeno, trifluoromethyl, nitro, amino, mono- or di-lower alkylamino, cyano, carbamoyl and carboxy; R is unsubstituted or substituted phenyl as defined by H-Ph, pyridyl, lower alkylpyridyl, or halogenopyridyl; R₁ is hydrogen, lower alkyl or lower (hydroxy, dialkylamino or H-Ph) -alkyl; and R₂ is hydrogen or lower alkyl; their 3-hydroxytautomers; lower alkanoyl, carbamoyl, mono- or di-lower alkylcarbamoyl derivatives of said (hydroxy or amino)-(phenyl or phenylene) compounds; and

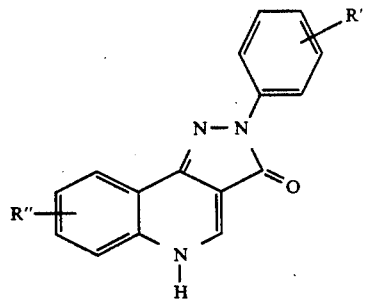

iii where R" is hydrogen, alkyl or alkoxy with up to 4 carbon atoms each, hydroxy, fluoro, chloro, bromo, or trifluoromethyl; and R' is hydrogen, o- or m-fluoro; or it is p-fluoro when R" is chloro.

Bull. Chem. Soc. Japan, 50: 3075 (Merchant and Shirali, 1977) discloses certain 5-methyloxazolo-[4,5-c]quinolin-4(5H)-ones of the formula:

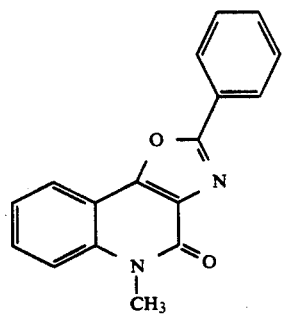

The compounds of the present invention differ from these compounds. These compounds are not oxazoloquinolinones and/or lack the various ring substituents of the compounds of the present invention.

SUMMARY OF THE INVENTION

This invention provides novel compounds of Formula I which interact with a GABAa binding site, the benzodiazepine receptor.

The invention provides pharmaceutical compositions comprising compounds of Formula I. The invention also provides compounds useful in enhancing alertness, treatment of seizure, anxiety, and sleep disorders, and treatment of benzodiazepine overdoses. Accordingly, a broad embodiment of the invention is directed to compounds of Formula I:

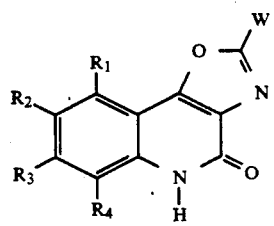

I and the pharmaceutically acceptable non-toxic salts thereof wherein:

$R_1$ and $R_4$ are the same or different and represent hydrogen, halogen, or straight or branched chain lower alkyl having 1-6 carbon atoms;

W is
  phenyl, 2- or 3-thienyl, or 2-, 3-, or 4-pyridyl; or
  phenyl, 2- or 3-thienyl, or 2-, 3-, or 4-pyridyl each of which is mono or disubstituted with halogen, hydroxy, straight or branched chain lower alkyl having 1-6 carbon atoms, straight or branched chain lower alkoxy having 1-6 carbon atoms, amino, or mono- or dialkylamino where each alkyl portion is straight or branched chain lower alkyl having 1-6 carbon atoms; and $R_2$ and $R_3$ are the same or different and represent
  hydrogen, halogen, hydroxy, straight or branched chain lower alkyl having 1-6 carbon atoms, amino, mono or dialkylamino where each alkyl portion is straight or branched chain lower alkyl having 1-6 carbon atoms; or
  $R_5$, $OR_5$, $COR_2R_5$, or $OCOR_5$, where $R_5$ is hydrogen, straight or branched chain lower alkyl having 1-6 carbon atoms, phenyl, or phenylalkyl where the alkyl portion is straight or branched chain lower alkyl having 1-6 carbon atoms; or
  —$CONR_6R_7$ or —$(CH_2)_nNR_6R_7$, where n is 0, 1, or 2, $R_6$ is hydrogen, straight or branched chain lower alkyl having 1-6 carbon atoms, and $R_7$ is hydrogen, straight or branched chain lower alkyl having 1-6 carbon atoms, phenyl, or phenylalkyl where the alkyl portion is straight or branched chain lower alkyl having 1-6 carbon atoms; or
  —$CONR_6R_7$ or —$(CH_2)_nNR_6R_7$, where n is 0, 1, or 2, and $NR_6R_7$ forms a heterocyclic group which is morpholyl, piperidyl, pyrrolidyl, or N-alkylpiperizyl where the alkyl portion is straight or branched chain lower alkyl having 1-6 carbon atoms; or
  —$NR_8CO_2R_9$ where $R_8$ and $R_9$ are the same or different and represent hydrogen, straight or branched chain lower alkyl having 1-6 carbon atoms, phenyl, or phenylalkyl where the alkyl portion is straight or branched chain lower alkyl having 1-6 carbon atoms, or
  —$C(OH)R_{10}R_{11}$ where $R_{10}$ and $R_{11}$ are the same or different and represent straight or branched chain lower alkyl having 1-6 carbon atoms, phenylalkyl where the alkyl portion is straight or branched chain lower alkyl having 1-6 carbon atoms.

These compounds are highly selective agonists, antagonists or inverse agonists for GABAa brain receptors or prodrugs of agonists, antagonists or inverse agonists for GABAa brain receptors. These compounds are useful in the diagnosis and treatment of anxiety, sleep, and seizure disorders, oversode with benzodiazepine drugs, and enhancement of memory.

DETAILED DESCRIPTION OF THE INVENTION

Figure 1A:
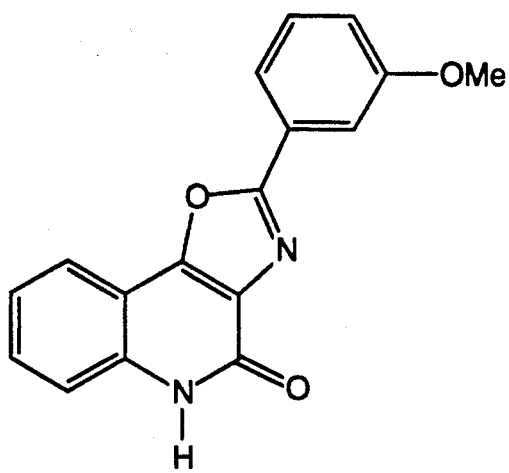
FIGS. 1A-C show representative oxazoloquinolinones of the present invention.

The novel compounds encompassed by the instant invention can be described by the following general formula I:

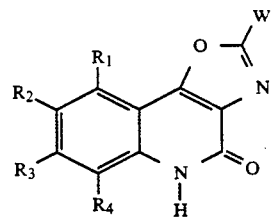

and the pharmaceutically acceptable non-toxic salts thereof wherein:

$R_1$ and $R_4$ are the same or different and represent hydrogen, halogen or straight or branched chain lower alkyl having 1-6 carbon atoms;

W is
  phenyl, 2- or 3-thienyl, or 2-, 3-, or 4-pyridyl; or
  phenyl, 2- or 3-thienyl, or 2-, 3-, or 4-pyridyl each of which is mono or disubstituted with halogen, hydroxy, straight or branched chain lower alkyl having 1-6 carbon atoms, straight or branched chain lower alkoxy having 1-6 carbon atoms, amino, or mono- or dialkylamino where each alkyl portion is straight or branched chain lower alkyl having 1-6 carbon atoms; and $R_2$ and $R_3$ are the same or different and represent
  hydrogen, halogen, hydroxy, straight or branched chain lower alkyl having 1-6 carbon atoms, amino, mono or dialkylamino where each alkyl portion is straight or branched chain lower alkyl having 1-6 carbon atoms; or
  $R_5$, $OR_5$, $COR_5$, $CO_2R_5$, or $OCOR_5$, where $R_5$ is hydrogen, straight or branched chain lower alkyl having 1-6 carbon atoms, phenyl, or phenylalkyl where the alkyl portion is straight or branched chain lower alkyl having 1-6 carbon atoms; or
  —$CONR_6R_7$ or —$(CH_2)_nNR_6R_7$, where n is 0, 1, or 2, $R_6$ is hydrogen, straight or branched chain lower alkyl having 1-6 carbon atoms, and $R_7$ is hydrogen, straight or branched chain lower alkyl having 1-6 carbon atoms, phenyl, or phenylalkyl where the alkyl portion is straight or branched chain lower alkyl having 1-6 carbon atoms; or
  —$CONR_6R_7$ or —$(CH_2)_nNR_6R_7$, where n is 0, 1, or 2, and $NR_6R_7$ forms a heterocyclic group which is morpholyl, piperidyl, pyrrolidyl, or N-alkylpiperizyl where the alkyl portion is straight or branched chain lower alkyl having 1-6 carbon atoms; or
  —$NR_8CO_2R_9$ where $R_8$ and $R_9$ are the same or different and represent hydrogen, straight or branched chain lower alkyl having 1-6 carbon atoms, phenyl, or phenylalkyl where the alkyl portion is straight or branched chain lower alkyl having 1-6 carbon atoms, or
  —$C(OH)R_{10}R_{11}$ where $R_{10}$ and $R_{11}$ are the same or different and represent straight or branched chain lower alkyl having 1-6 carbon atoms, phenylalkyl where the alkyl portion is straight or branched chain lower alkyl having 1-6 carbon atoms.

In addition, the present invention encompasses compounds of Formula II.

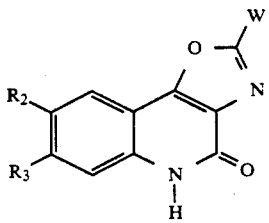

wherein:
W is
phenyl, 2- or 3-thienyl, or 2-, 3-, or 4-pyridyl; or
phenyl, 2- or 3-thienyl, or 2-, 3-, or 4-pyridyl each of which is mono or disubstituted with halogen, hydroxy, straight or branched chain lower alkyl having 1-6 carbon atoms, straight or branched chain lower alkoxy having 1-6 carbon atoms, amino, or mono- or dialkylamino where each alkyl portion is straight or branched chain lower alkyl having 1-6 carbon atoms; and $R_2$ and $R_3$ are the same or different and represent
hydrogen, halogen, hydroxy, straight or branched chain lower alkyl having 1-6 carbon atoms, amino, mono or dialkylamino where each alkyl portion is straight or branched chain lower alkyl having 1-6 carbon atoms; or
$R_5$, $OR_5$, $COR_5$, $CO_2R_5$, or $OCOR_5$, where $R_5$ is hydrogen, straight or branched chain lower alkyl having 1-6 carbon atoms, phenyl, or phenylalkyl where the alkyl portion is straight or branched chain lower alkyl having 1-6 carbon atoms.

The present invention also encompases compounds of Formula III:

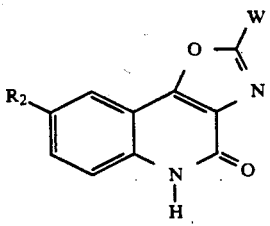

wherein:
W is
phenyl, 2- or 3-thienyl, or 2-, 3-, or 4-pyridyl; or
phenyl, 2- or 3-thienyl, or 2-, 3-, or 4-pyridyl each of which is mono or disubstituted with halogen, hydroxy, straight or branched chain lower alkyl having 1-6 carbon atoms, straight or branched chain lower alkoxy having 1-6 carbon atoms, amino, or mono- or dialkylamino where each alkyl portion is straight or branched chain lower alkyl having 1-6 carbon atoms; and $R_2$ represents
hydrogen, halogen, hydroxy, straight or branched chain lower alkyl having 1-6 carbon atoms, straight or branched chain lower alkoxy having 1-6 carbon atoms, amino, or mono- or dialkylamino where each alkyl is straight or branched chain lower alkyl having 1-6 carbon atoms.

Non-toxic pharmaceutical salts include salts of acids such as hydrochloric, phosphoric, hydrobromic, sulfuric, sulfinic, formic, toluene sulfonic, hydroiodic, acetic and the like. Those skilled in the art will recognize a wide variety of non-toxic pharmaceutically acceptable addition salts.

Figure 1B:
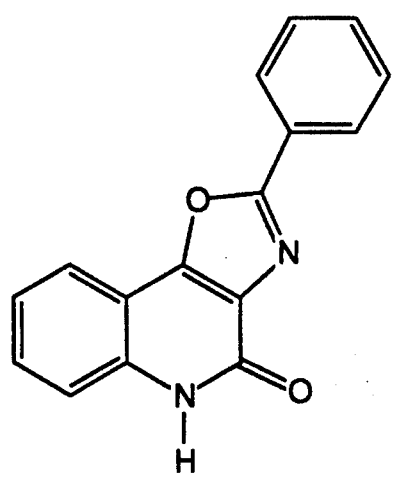
Figure 1C:
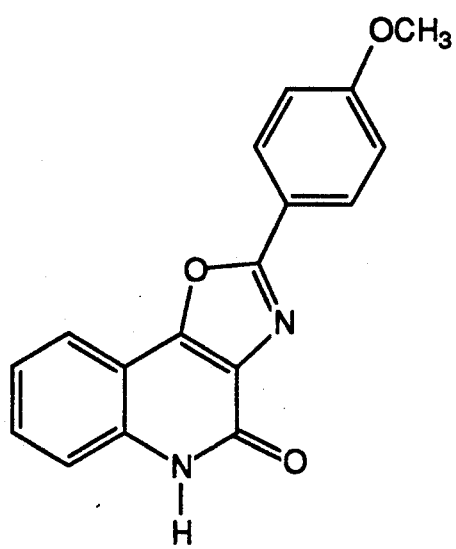

Representative compounds of the present invention, which are encompassed by Formula I, include, but are not limited to the compounds in FIGS. 1A-C and their pharmaceutically acceptable salts. The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By lower alkyl in the present invention is meant straight or branched chain alkyl groups having 1-6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By lower alkoxy in the present invention is meant straight or branched chain alkoxy groups having 1-6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By halogen in the present invention is meant fluorine, bromine, chlorine, and iodine.

By N-alkylpiperizyl in the invention is meant radicals of the formula:

where R is a straight or branched chain lower alkyl as defined above.

The pharmaceutical utility of compounds of this invention are indicated by the following assay for GABAa receptor activity.

Assays are carried out as described in Thomas and Tallman (J. Bio. Chem. 156: 9838-9842, J. Neurosci. 3:433-440, 1983). Rat cortical tissue is dissected and homogenized in 25 volumes (w/v) of 0.05M Tris HCl buffer (pH 7.4 at 4° C.). The tissue homogenate is centrifuged in the cold (4° C.) at 20,000×g for 20 minutes. The supernatant is decanted and the pellet is rehomogenized in the same volume of buffer and again centrifuged at 20,000× g. The supernatant is decanted and the pellet is frozen at −20° C. overnight. The pellet is then thawed and rehomogenized in 25 volume (original wt/vol) of buffer and the procedure is carried out twice. The pellet is finally resuspended in 50 volumes (w/vol of 0.05M Tris HCl buffer (pH 7.4 at 40° C.).

Incubations contain 100 ml of tissue homogenate, 100 ml of radioligand 0.5 nM ($^3$H-RO15-1788[$^3$H-Flumazenil] specific activity 80 Ci/mmol), drug or blocker and buffer to a total volume of 500 ml. Incubations are carried for 30 min at 4° C. then are rapidly filtered through GFB filters to separate free and bound ligand. Filters are washed twice with fresh 0.05M Tris HCl buffer (pH 7.4 at 4° C.) and counted in a liquid scintillation counter. 1.0 mM diazepam is added to some tubes to determine nonspecific binding. Data are collected in triplicate determinations, averaged and % inhibition of total specific binding is calculated. Total Specific Binding=Total−Nonspecific. In some cases, the amounts of unlabeled drugs is varied and total displacement curves of binding are carried out. Data are converted to a form for the calculation of $IC_{50}$ and Hill Coefficient (nH). Data for the compounds of this invention are listed in Table I.

TABLE I

| Compound Number[1] | $IC_{50}$ ($\mu$M) |
|---|---|
| 1 | 0.600 |
| 2 | 0.095 |
| 4 | 0.125 |

[1]Compound numbers relate to compounds shown in FIGS. 1A-C.

Compounds 1, 2 and 4 are particularly preferred embodiments of the present invention because of their potency in binding to the GABAa receptor. A prior art compound disclosed in Bull. Chem. Soc. Japan, 50: 3075 (1977), 5-methyl-2-phenyl-oxazolo[4,5-c]quinolin-4(5H)-one, was prepared and assayed according to the assay described above; this compound was inactive in the assay with an $IC_{50}$ of about 50.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Illustrations of the preparation of compounds of the present invention are given in Scheme I. Those having skill in the art will recognize that the starting materials may be varied and additional steps employed to produce compounds encompassed by the present invention, as demonstrated by the following examples.

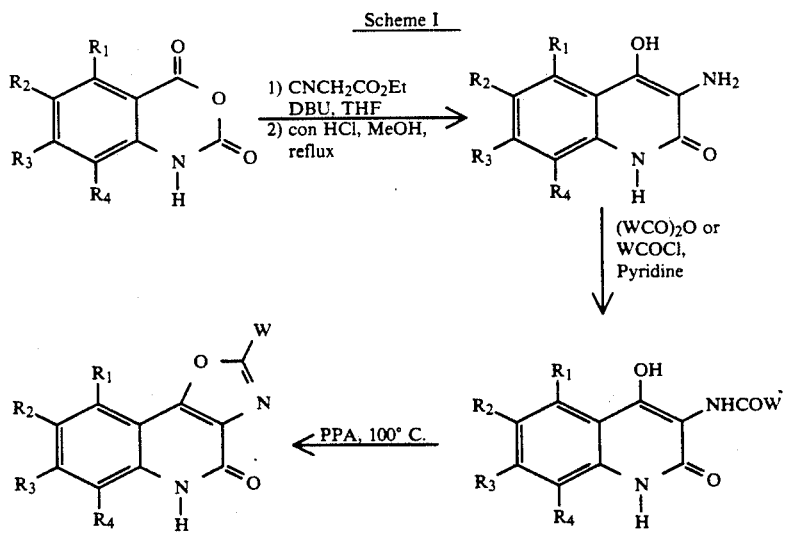

Scheme I wherein:
$R_1$ and $R_4$ are the same or different and represent hydrogen, halogen or straight or branched chain lower alkyl having 1-6 carbon atoms;

W is
phenyl, 2- or 3-thienyl, or 2-, 3-, or 4-pyridyl; or
phenyl, 2- or 3-thienyl, or 2-, 3-, or 4-pyridyl each of which is mono or disubstituted with halogen, hydroxy, straight or branched chain lower alkyl having 1-6 carbon atoms, straight or branched chain lower alkoxy having 1-6 carbon atoms, amino, or mono- or dialkylamino where each alkyl portion is straight or branched chain lower alkyl having 1-6 carbon atoms; and $R_2$ and $R_3$ are the same or different and represent hydrogen, halogen, hydroxy, straight or branched chain lower alkyl having 1-6 carbon atoms, amino, mono or dialkylamino where each alkyl portion is straight or branched chain lower alkyl having 1-6 carbon atoms; or $R_5$, $OR_5$, $COR_5$, $CO_2R_5$, or $OCOR_5$, where $R_5$ is hydrogen, straight or branched chain lower alkyl having 1-6 carbon atoms, phenyl, or phenylalkyl where the alkyl portion is straight or branched chain lower alkyl having 1-6 carbon atoms; or —$CONR_6R_7$ or —$(CH_2)_nNR_6R_7$, where n is 0, 1, or 2, $R_6$ is hydrogen, straight or branched chain lower alkyl having 1-6 carbon atoms, and $R_7$ is hydrogen, straight or branched chain lower alkyl having 1-6 carbon atoms, phenyl, or phenylalkyl where the alkyl portion is straight or branched chain lower alkyl having 1-6 carbon atoms; or —$CONR_6R_7$ or —$(CH_2)_nNR_6R_7$, where n is 0, 1, or 2, and $NR_6R_7$ forms a heterocyclic group which is morpholyl, piperidyl, pyrrolidyl, or N-alkylpiperizyl where the alkyl portion is straight or branched chain lower alkyl having 1-6 carbon atoms; or —$NR_8CO_2R_9$ where $R_8$ and $R_9$ are the same or different and represent hydrogen, straight or branched chain lower alkyl having 1-6 carbon atoms, phenyl, or phenylalkyl where the alkyl portion is straight or branched chain lower alkyl having 1-6 carbon atoms, or —C(OH)R$_{10}$R$_{11}$ where R$_{10}$ and R$_{11}$ are the same or different and represent straight or branched chain lower alkyl having 1-6 carbon atoms, phenylalkyl where the alkyl portion is straight or branched chain lower alkyl having 1-6 carbon atoms.

EXAMPLE I

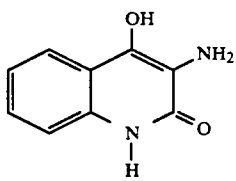

Isatoic anhydride (81.6 g, 0.5 mol) was added in portions over 1 h to a well stirred mixture of ethyl isocyanoacetate (22.7 mL, 0.25 mol) and DBU (74.8 mL, 0.5 mol) in dry tetrahydrofuran (550 mL). After 63 h at room temperature, the reaction mixture was cooled in an ice bath, neutralized with acetic acid and 500 mL of water was added. The resulting precipitate was collected and washed with water and methanol. This precipate was treated with concentrated hydrochloric acid (140 mL) and methanol (690 mL) and refluxed for 1 h. The reaction mixture was concentrated in vacuo and the residue treated with ethanol to afford 3-Amino-quinoxalin-2,4-diol monohydrochloride as a bone colored solid.

EXAMPLE II

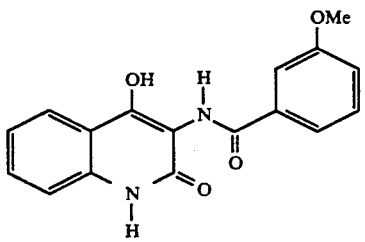

A mixture of 3-Amino-quinoxalin-2,4-diol monohydrochloride (424 mg, 2 mmol) and m-Methoxybenzoic anhydride (571 mg, 2 mmol) in dry pyridine (5 mL) was kept at room temperature for 16 h. The reaction mixture was poured onto ice water and the product was collected to afford 3-(3-Methoxybenzamido)-quinoxalin-2,4-diol as a cream colored solid.

EXAMPLE III

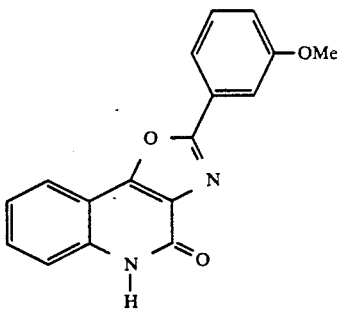

(Compound 1)

A mixture of 3-(3-Methoxybenzamido)-quinoxalin-2,4-diol (505 mg, 1.6 mmol) and polyphosphoric acid (5 g) was heated at 100° C. for 4.5 h. The mixture was poured onto ice and the product was collected. This material was recrystallized from ethanol to afford 2-(3-Methoxyphenyl)-oxazolo[4,5-c]quinolin-4(5H)-one (Compound 1) as colorless crystals melting at 322°-324° C.(dec).

EXAMPLE IV

The following compounds were prepared essentially according to Examples I-III:
(a) 2-Phenyl-oxazolo[4,5-c]quinolin-4(5H)-one (Compound 2), m.p. 345°-346° C.
(b) 2-(4-Ethoxyphenyl)-oxazolo[4,5-c]quinolin-4(5H)-one (Compound 3), m.p. 347°-348° C.
(c) 2-(4-Methoxyphenyl)-oxazolo[4,5-c]quinolin-4(5H)-one (Compound 4), m.p. 320°-322° C.(dec).
(d) 2-(4-Methylphenyl)-oxazolo[4,5-c]quinolin-4(5H)-one (Compound 5).
(d) 2-(4-Fluorophenyl)-oxazolo[4,5-c]quinolin-4(5H)-one (Compound 6).
(f) 2-(3-Fluorophenyl)-oxazolo[4,5-c]quinolin-4(5H)-one (Compound 7).
(g) 2-(4-Chlorophenyl)-oxazolo[4,5-c]quinolin-4(5H)-one (Compound 8).
(h) 2-(3-Methylphenyl)-oxazolo[4,5-c]quinolin-4(5H)-one (Compound 9).
(i) 2-(2-Fluorophenyl)-oxazolo[4,5-c]quinolin-4(5H)-one (Compound 10).
(j) 2-(3-Chlorophenyl)-oxazolo[4,5-c]quinolin-4(5H)-one (Compound 11).
(k) 2-(2-Thienyl)-oxazolo[4,5-c]quinolin-4(5H)-one (Compound 12).
(l) 2-(5-Methyl-2-thienyl)-oxazolo[4,5-c]quinolin-4(5H)-one (Compound 13).
(m) 2-(4-Fluorophenyl)-8-bromo-oxazolo[4,5-c]quinolin-4(5H)-one (Compound 14).
(n) 2-(4-Ethylphenyl)-oxazolo[4,5-c]quinolin-4(5H)-one (Compound 11), m.p. 322°-324° C.

EXAMPLE IV

A compound disclosed in Bull. Chem. Soc. Japan, 50: 3075 (Merchant and Shirali, 1977), 5-methyl-2-phenyl-oxazolo[4,5-c]quinolin-4(5H)-one, was prepared essentially according to Examples I-III and gave a melting point of 218°-220° C. In the assay described above, this compound exibited no activity with an IC$_{50}$ of about 50.

The invention and the manner and process of making and using it, are now described in such full, clear, concise and exact terms as to enable any person skilled in

What is claimed is:

1. A compound of the formula:

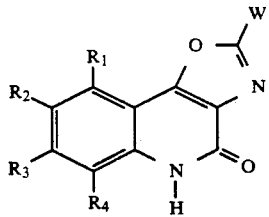

and the pharmaceutically acceptable non-toxic salts thereof $R_1$ and $R_4$ are the same or different and represent hydrogen, halogen or straight or branched chain lower alkyl having 1-6 carbon atoms;

W is 2- or 3-thienyl, or 2-, 3-, or 4-pyridyl; or phenyl, 2- or 3-thienyl, or 2-, 3-, or 4-pyridyl each of which is mono or disubstituted with halogen, hydroxy, straight or branched chain lower alkyl having 1-6 carbon atoms, straight or branched chain lower alkoxy having 1-6 carbon atoms, amino, or mono- or dialkylamino where each alkyl portion is straight or branched chain lower alkyl having 1-6 carbon atoms; and $R_2$ and $R_3$ are the same or different and represent hydrogen, halogen, hydroxy, straight or branched chain lower alkyl having 1-6 carbon atoms, amino, mono or dialkylamino where each alkyl portion is straight or branched chain lower alkyl having 1-6 carbon atoms; or $OR_5$, $COR_5$, $CO_2R_5$, or $OCOR_5$, where $R_5$ is hydrogen, straight or branched chain lower alkyl having 1-6 carbon atoms, phenyl, or phenylalkyl where the alkyl portion is straight or branched chain lower alkyl having 1-6 carbon atoms; or —$CONR_6R_7$ or —$(CH_2)_nNR_6R_7$, where n is 0, 1, or 2, $R_6$ is hydrogen, straight or branched chain lower alkyl having 1-6 carbon atoms, and $R_7$ is hydrogen, straight or branched chain lower alkyl having 1-6 carbon atoms, phenyl, or phenylalkyl where the alkyl portion is straight or branched chain lower alkyl having 1-6 carbon atoms; or —$CONR_6R_7$ or —$(CH_2)_nNR_6R_7$, where n is 0, 1, or 2, and $NR_6R_7$ forms a heterocyclic group which is morpholyl, piperidyl, pyrrolidyl, or N-alkylpiperazyl where the alkyl portion is straight or branched chain lower alkyl having 1-6 carbon atoms; or —$NR_8CO_2R_9$ where $R_8$ and $R_9$ are the same or different and represent hydrogen, straight or branched chain lower alkyl having 1-6 carbon atoms, phenyl, or phenylalkyl where the alkyl portion is straight or branched chain lower alkyl having 1-6 carbon atoms, or —$C(OH)R_{10}R_{11}$ where $R_{10}$ and $R_{11}$ are the same or different and represent straight or branched chain lower alkyl having 1-6 carbon atoms, phenylalkyl where the alkyl portion is straight or branched chain lower alkyl having 1-6 carbon atoms.

2. A compound according to claim 1, which is:

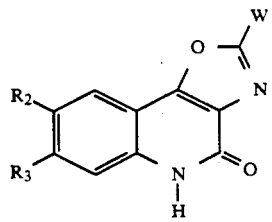

wherein:

W is 2- or 3-thienyl, or 2-, 3-, or 4-pyridyl; or phenyl, 2- or 3-thienyl, or 2-, 3-, or 4-pyridyl each of which is mono or disubstituted with halogen, hydroxy, straight or branched chain lower alkyl having 1-6 carbon atoms, straight or branched chain lower alkoxy having 1-6 carbon atoms, amino, or mono- or dialkylamino where each alkyl portion is straight or branched chain lower alkyl having 1-6 carbon atoms; and $R_2$ and $R_3$ are the same or different and represent hydrogen, halogen, hydroxy, straight or branched chain lower alkyl having 1-6 carbon atoms, amino, mono or dialkylamino where each alkyl portion is straight or branched chain lower alkyl having 1-6 carbon atoms; or $OR_5$, $COR_5$, $CO_2R_5$, or $OCOR_5$, where $R_5$ is hydrogen, straight or branched chain lower alkyl having 1-6 carbon atoms, phenyl, or phenylalkyl where the alkyl portion is straight or branched chain lower alkyl having 1-6 carbon atoms.

3. A compound according to claim 1, which is:

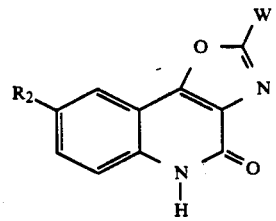

wherein:

W is 2- or 3-thienyl, or 2-, 3-, or 4-pyridyl; or phenyl, 2- or 3-thienyl, or 2-, 3-, or 4-pyridyl each of which is mono or disubstituted with halogen, hydroxy, straight or branched chain lower alkyl having 1-6 carbon atoms, straight or branched chain lower alkoxy having 1-6 carbon atoms, amino, or mono- or dialkylamino where each alkyl portion is straight or branched chain lower alkyl having 1-6 carbon atoms; and $R_2$ represents hydrogen, halogen, hydroxy, straight or branched chain lower alkyl having 1-6 carbon atoms, straight or branched chain lower alkoxy having 1-6 carbon atoms, amino, or mono- or dialkylamino where each alkyl is straight or branched chain lower alkyl having 1-6 carbon atoms.

4. A compound according to claim 1, wherein $R_2$ is bromine.

5. A compound according to claim 1, wherein W is 3- or 4-methoxyphenyl.

6. A compound according to claim 1, wherein W is 2-fluorophenyl.

7. A compound according to claim 1, which is 2-(3-Methoxyphenyl)-oxazolo[4,5-c]quinolin-4(5H)-one.

8. A compound according to claim 1, which is 2-(4-Methoxyphenyl)-oxazolo[4,5-c]quinolin-4(5H)-one.

9. A compound according to claim 1, which is 2-(4-Ethoxyphenyl)-oxazolo[4,5-c]quinolin-4(5H)-one.

10. A compound according to claim 1, which is 2-(4-Methylphenyl)-oxazolo[4,5-c]quinolin-4(5H)-one.

11. A compound according to claim 1, which is 2-(4-Fluorophenyl)-oxazolo[4,5-c]quinolin-4(5H)-one.

12. A compound according to claim 1, which is 2-(3-Fluorophenyl)-oxazolo[4,5-c]quinolin-4(5H)-one.

13. A compound according to claim 1, which is 2-(4-Chlorophenyl)-oxazolo[4,5-c]quinolin-4(5H)-one.

14. A compound according to claim 1, which is 2-(3-Methylphenyl)-oxazolo[4,5-c]quinolin-4(5H)-one.

15. A compound according to claim 1, which is 2-(2-Fluorophenyl)-oxazolo[4,5-c]quinolin-4(5H)-one.

16. A compound according to claim 1, which is 2-(3-Chlorophenyl)-oxazolo[4,5-c]quinolin-4(5H)-one.

17. A compound according to claim 1, which is 2-(2-Thienyl)-oxazolo[4,5-c]quinolin-4(5H)-one.

18. A compound according to claim 1, which is 2-(5-Methyl-2-thienyl)-oxazolo[4,5-c]quinolin-4(5H)-one.

19. A compound according to claim 1, which is 2-(4-Fluorophenyl)-8-bromo-oxazolo[4,5-c]quinolin-4(5H)-one.

20. A compound according to claim 1, which is 2-(4-Ethylphenyl)-oxazolo[4,5-c]quinolin-4(5H)-one.

21. A pharmaceutical composition suitable for treatment of conditions in mammals mediated by the use of compounds which selectively bind to GABA receptors comprising a non-toxic pharmaceutically acceptable carrier and a compound of the formula:

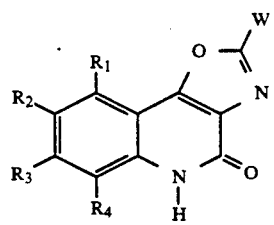

wherein:

$R_1$ and $R_4$ are the same or different and represent hydrogen, halogen or straight or branched chain lower alkyl having 1-6 carbon atoms;

W is
phenyl, 2- or 3-thienyl, or 2-, 3-, or 4-pyridyl; or
phenyl, 2- or 3-thienyl, or 2-, 3-, or 4-pyridyl each of which is mono or disubstituted with halogen, hydroxy, straight or branched chain lower alkyl having 1-6 carbon atoms, straight or branched chain lower alkoxy having 1-6 carbon atoms, amino, or mono- or dialkylamino where each alkyl portion is straight or branched chain lower alkyl having 1-6 carbon atoms: and $R_2$ and $R_3$ are the same or different and represent hydrogen, halogen, hydroxy, straight or branched chain lower alkyl having 1-6 carbon atoms, amino, mono or dialkylamino where each alkyl portion is straight or branched chain lower alkyl having 1-6 carbon atoms; or $OR_5$, $COR_5$, $CO_2R_5$, or $OCOR_5$, where $R_5$ is hydrogen, straight or branched chain lower alkyl having 1-6 carbon atoms, phenyl, or phenylalkyl where the alkyl portion is straight or branched chain lower alkyl having 1-6 carbon atoms; or —$CONR_6R_7$ or —$(CH_2)_nNR_6R_7$, where n is 0, 1, or 2, $R_6$ is hydrogen, straight or branched chain lower alkyl having 1-6 carbon atoms, and $R_7$ is hydrogen, straight or branched chain lower alkyl having 1-6 carbon atoms, phenyl, or phenylalkyl where the alkyl portion is straight or branched chain lower alkyl having 1-6 carbon atoms; or —$CONR_6R_7$ or —$(CH_2)_nNR_6R_7$, where n is 0, 1, or 2, and $NR_6R_7$ forms a heterocyclic group which is morpholyl, piperidyl, pyrrolidyl, or N-alkylpiperizyl where the alkyl portion is straight or branched chain lower alkyl having 1-6 carbon atoms; or —$NR_8CO_2R_9$ where $R_8$ and $R_9$ are the same or different and represent hydrogen, straight or branched chain lower alkyl having 1-6 carbon atoms, phenyl, or phenylalkyl where the alkyl portion is straight or branched chain lower alkyl having 1-6 carbon atoms, or —$C(OH)R_{10}R_{11}$ where $R_{10}$ and $R_{11}$ are the same or different and represent straight or branched chain lower alkyl having 1-6 carbon atoms, phenylalkyl where the alkyl portion is straight or branched chain lower alkyl having 1-6 carbon atoms.

22. A pharmaceutical composition according to claim 21, where the compound is 2-Phenyl-oxazolo[4,5-c]quinolin-4(5H)-one.

* * * * *